United States Patent
Fitzgibbons et al.

(10) Patent No.: US 11,653,872 B2
(45) Date of Patent: May 23, 2023

(54) PATIENT SUPPORT APPARATUS HAVING VITAL SIGNS AND SEPSIS DISPLAY APPARATUS

(71) Applicant: Hill-Rom Services, Inc., Batesville, IN (US)

(72) Inventors: Stacey A. Fitzgibbons, DeWitt, NY (US); Jotpreet Chahal, Fayetteville, NY (US); Craig M. Meyerson, Syracuse, NY (US)

(73) Assignee: Hill-Rom Services, Inc., Batesville, IN (US)

( * ) Notice: Subject to any disclaimer, the term of this patent is extended or adjusted under 35 U.S.C. 154(b) by 543 days.

(21) Appl. No.: 16/795,666

(22) Filed: Feb. 20, 2020

(65) Prior Publication Data
US 2020/0275877 A1    Sep. 3, 2020

Related U.S. Application Data

(60) Provisional application No. 62/811,565, filed on Feb. 28, 2019.

(51) Int. Cl.
*G16H 10/60* (2018.01)
*G16H 50/30* (2018.01)
*A61B 5/00* (2006.01)
*A61B 5/0205* (2006.01)

(52) U.S. Cl.
CPC .......... *A61B 5/412* (2013.01); *A61B 5/02055* (2013.01); *A61B 5/706* (2013.01); *A61B 5/7275* (2013.01); *A61B 5/742* (2013.01); *G16H 10/60* (2018.01); *G16H 50/30* (2018.01)

(58) Field of Classification Search
CPC ..... A61B 5/412; A61B 5/02055; A61B 5/706; A61B 5/7275; A61B 5/742; G16H 10/60; G16H 50/30

USPC .......................................................... 600/301
See application file for complete search history.

(56) References Cited

U.S. PATENT DOCUMENTS

| | | | |
|---|---|---|---|
| 9,968,289 B2 | 5/2018 | Newberry | |
| 10,517,784 B2 | 12/2019 | Zerhusen et al. | |
| 11,504,011 B1* | 11/2022 | Jain | A61B 5/1118 |
| 11,545,271 B2* | 1/2023 | Barkol | H04L 51/046 |
| 2010/0324380 A1 | 12/2010 | Perkins et al. | |
| 2013/0002420 A1 | 1/2013 | Perkins et al. | |
| 2013/0296720 A1 | 11/2013 | McKinley et al. | |
| 2014/0005502 A1* | 1/2014 | Klap | A61B 5/1116 600/300 |
| 2014/0323816 A1 | 10/2014 | Soderberg et al. | |
| 2015/0025329 A1* | 1/2015 | Amarasingham | G16H 50/20 600/300 |

(Continued)

FOREIGN PATENT DOCUMENTS

EP    3345537 A1    7/2018

OTHER PUBLICATIONS

European Search Report from the European Patent Office for European Application No. 20157960.4, dated Apr. 8, 2020, 9 pages total.

*Primary Examiner* — Michael Tomaszewski
*Assistant Examiner* — Rachael Sojin Stone
(74) *Attorney, Agent, or Firm* — Barnes & Thornburg LLP

(57) ABSTRACT

A patient support apparatus includes a sensor capable of detecting vital signs and includes structures for monitoring the vital signs and providing local and/or remote indications to caregivers if the vital signs fall outside of acceptable limits.

20 Claims, 6 Drawing Sheets

(56) References Cited

U.S. PATENT DOCUMENTS

| | | |
|---|---|---|
| 2018/0184984 A1 | 7/2018 | Zerhusen et al. |
| 2018/0289312 A1 | 10/2018 | Perkins et al. |
| 2019/0051383 A1 | 2/2019 | Sherwin et al. |
| 2019/0307405 A1 | 10/2019 | Terry et al. |
| 2019/0336085 A1 | 11/2019 | Kayser et al. |
| 2020/0066415 A1 | 2/2020 | Hettig et al. |

\* cited by examiner

PATIENT SUPPORT APPARATUS HAVING VITAL SIGNS AND SEPSIS DISPLAY APPARATUS

PRIORITY CLAIM

This application claims priority under 35 U.S.C. § 119(e) to U.S. Provisional Application No. 62/811,565, filed Feb. 28, 2019, which is expressly incorporated by reference herein.

BACKGROUND

The present disclosure is related to patient support apparatuses having alerting capabilities. More specifically, the present disclosure is related to patient support apparatuses that include sensors for monitoring vital signs and structures for alerting caregivers when the vital signs are unacceptable.

Patients in healthcare facilities may have a risk of developing sepsis during their stay. Sepsis is a negative condition or response that a person's body has to an infection. Sepsis results when a person's immune system stops fighting or has an insufficient response to an infection Sepsis risk assessments of patients oftentimes take place on a sporadic basis with prolonged periods transpiring between the assessments. Furthermore, the results of risk assessments are sometimes only available at a limited number of locations in the healthcare facility such as at an electronic medical records computer or at a computer of a master nurse station. Accordingly, there is a need in the healthcare field to have more timely information regarding the risk assessments of sepsis and there is a need for the risk assessment information to be more readily available to caregivers.

SUMMARY

The present application discloses one or more of the features recited in the appended claims and/or the following features which, alone or in any combination, may comprise patentable subject matter:

In a first aspect of the present disclosure, a patient support apparatus includes a sensor, a controller, and a sepsis-status notification system. The sensor provides signals indicative of vital signs of a patient positioned on the patient support apparatus. The controller is coupled to the sensor and includes a processor and a memory device, the memory device including instructions that, when executed, cause the controller to receive the first and second sensor signals, compare the signals to pre-established acceptable limits, calculate a sepsis risk assessment score based on the signals, and, if the sepsis risk assessment score is at or above a predetermined value, output a command signal. The sepsis-status notification system responds to the command signal from the controller to display a first visual indication that shows that the patient is septic and display second visual indication that shows a status of a sepsis protocol administration.

In some embodiments, the vital signs include at least one of temperature, respiratory rate, heart rate, and blood pressure.

In some embodiments, the first visual indication includes an alert that shows the patient is septic and second visual indication includes a timer that measures how long the patient has been septic.

In some embodiments, the timer is a countdown timer that displays an amount of time remaining in the sepsis protocol administration.

In some embodiments, the controller is configured to communicate with an external nurse call station and the visual indications are transmitted for display at a nurse call station.

In some embodiments, the second visual indication further includes an iconic representation of the procedures performed on the patient since sepsis was determined to be present.

In some embodiments, at least one of the first and the second visual indications includes a projection of a light on a floor around the patient support apparatus.

In some embodiments, the at least one of the first and the second visual indications includes an alert message on an interface coupled to the patient support apparatus.

In some embodiments, the alert message includes at least one of a textual indication that the patient is septic, an iconic representation that the patient is septic, and a timer.

In some embodiments, the controller is configured to communicate with an electronic medical record system to receive information from the electronic medical record system indicative of a medical history of a patient supported on the patient support apparatus.

In some embodiments, the controller is configured to compare the signals provided by the sensor to a list of predetermined conditions stored in the electronic medical record system to determine if the patient is septic.

In some embodiments, the controller is configured to provide the command signal if at least one of the vital signs deviates from acceptable limits and at least one of the predetermined conditions is present in the patient's electronic medical record.

In some embodiments, the controller is configured to compare the predetermined conditions to pre-established acceptable limits.

In some embodiments, the controller is configured to provide the command signal when at least one vital sign deviates from an acceptable limit and at least one predetermined condition deviates from the acceptable limit.

In some embodiments, the predetermined condition includes at least one of low blood pressure and a change in mental status.

In some embodiments, at least one of the first and the second visual indications includes an indicator panel that has a first color when no command signal is provided and has a second color, different from the first color when the command signal is provided.

In some embodiments, the controller is configured to communicate with an external device and display the at least one of the first and the second visual indications that the patient is septic on a screen of the external device.

In some embodiments, the sensor simultaneously detects a first vital sign and a second vital sign.

In some embodiments, the patient support apparatus includes a plurality of sensors each simultaneously detecting at least one vital sign of the patient.

In some embodiments, the plurality of sensors each detects both the first vital sign and the second vital sign.

In some embodiments, the controller is configured to receive signals from the plurality of sensors indicative of the position of a patient supported on the patient support apparatus, the controller is configured to utilize the position of the patient to determine whether to disregard the vital sign information from one of the plurality of sensors.

In some embodiments, the controller is configured to prompt a user to suspend the operation of the notification system based on the position of the patient.

In some embodiments, the notification system is configured to project the first visual indication to a surface spaced apart from the patient support apparatus.

In some embodiments, the first visual indication is simultaneously displayed at a surface of the patient support apparatus and projected onto the surface spaced apart from the patient support apparatus.

In some embodiments, the first visual indication is projected to the surface spaced apart from the patient support apparatus by a projector located on the patient support apparatus.

In some embodiments, displaying the first iconic representation in a first manner comprises displaying the first iconic representation in a first color and displaying the first iconic representation in a second manner comprises displaying the first iconic representation in a second color different than the first color.

In some embodiments, providing the visual indication includes simultaneously displaying a first iconic representation of the component on a surface of the patient support apparatus in a first color and projecting the first iconic representation of the component on the surface spaced apart from the patient support apparatus in the first color.

In some embodiments, the surface spaced apart from the patient support apparatus is the surface of a floor, the first iconic representation being projected to a position that is not directly below any portion of the patient support apparatus.

In a second aspect of the present disclosure, a patient support apparatus includes a first sensor, a second sensor, a controller, and a notification system. The first sensor provides a first signal indicative of a first vital sign of a patient supported on the patient support apparatus and a second sensor provides a second signal indicative of a second vital sign of the patient different than the first vital sign indicated by the first sensor. The controller is coupled to the sensors and includes a processor and a memory device, the memory device including instructions that, when executed, cause the controller to receive the first and second sensor signals, analyze an electronic medical record storing patient information for the patient, compare the signals and the patient information to pre-established acceptable limits, calculate a sepsis risk assessment score based on the signals and the patient information, and, if the sepsis risk assessment score is at or above a predetermined value, output a command signal. The notification system responds to the command signal from the controller to provide at least one visual indication that shows that the patient is septic.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION

Figure 1:
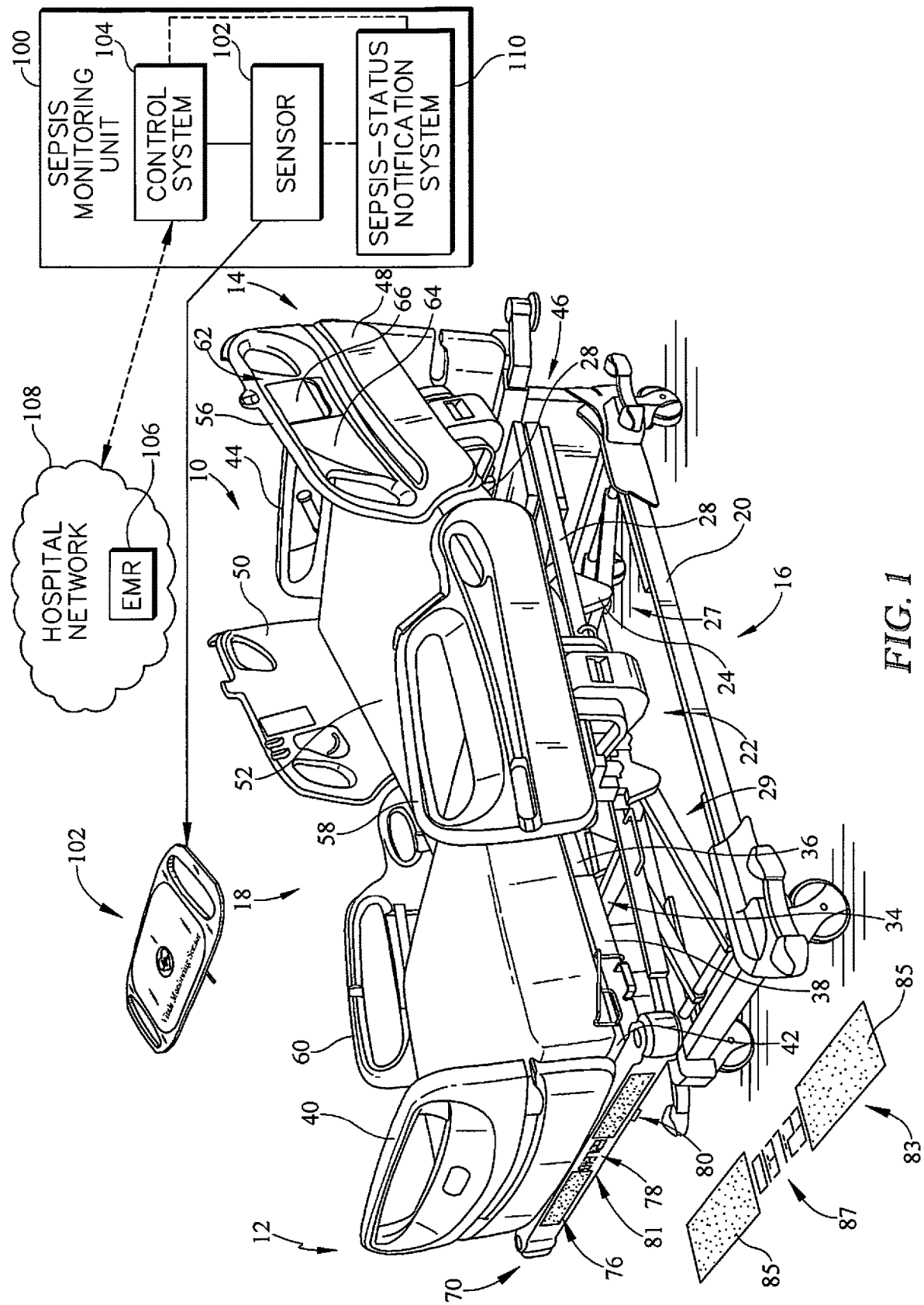
FIG. 1 is a perspective view of a patient support apparatus including a sepsis monitoring unit according to the present disclosure.

Referring to FIG. 1, a patient support apparatus 10 is illustratively embodied as a hospital bed 10. The hospital bed 10 includes an integrated sepsis monitoring unit 100 including a sepsis-status notification system 110. The sepsis monitoring unit 100 is configured to utilize data from a multitude of sources and, when appropriate, instruct the sepsis-status notification system 110 to provide an indication that the patient is at-risk for sepsis or has been diagnosed with sepsis. If the patient is diagnosed with sepsis, the sepsis-status notification system 110 is also configured to monitor a status of a sepsis protocol administration and provide an indication of that status.

The sepsis protocol includes a list of actions or procedures that should be administered to the patient within a three hour period and a six hour period beginning at the time the patient is diagnosed with sepsis or otherwise determined to be septic. For example, within the three hour protocols and timeframe, the following actions should be taken: 1) obtain blood cultures, 2) obtain a lactate measurement, 3) administer broad spectrum antibiotics, and 4) administer fluids crystalloid. Within a six hour protocol and timeframe, the following additional actions should be taken: 1) administration of vasopressors for non-responsive resuscitation, 2) maintaining adequate central venous pressure (CVP) and mixed venous oxygen content (CvO2) levels, and 3) obtaining a second lactate measurement if the first lactate measurement was high. Compliance with the sepsis protocols can increase the patient's chance of survival after being diagnosed with sepsis. The sepsis-status notification system 110 is configured to increase compliance with the protocols by notifying the caregiver and others near the patient if the patient is at-risk or diagnosed with sepsis, an amount of time that has passed, and a status of the actions that need to be completed for compliance with the protocols.

Sepsis may be detected using risk assessments that may vary between each healthcare facility. Some non-limiting examples of scores used to determine if a patient is at-risk for sepsis include a quick sequential (sepsis-related) organ failure assessment score (qSOFA) and/or systematic inflammatory response syndrome score (SIRS). Each method includes a set of criteria such as vital signs and/or other conditions that are defined by pre-established acceptable limits and are triggered when the patient deviates from those acceptable limits. Other examples of assessments or tests used to determine if a patient is at risk for sepsis are described in U.S. Provisional Patent Appl. No. 62/655,385, filed Apr. 10, 2018, which is expressly incorporated by reference herein. The sepsis-status notification system 110 may be programmed to operate with any assessment, test, or score criteria relating to sepsis including those that evolve as medical procedures advance.

When determining the patient's qSOFA or SIRS score, a point is assigned for each vital sign and/or other medical condition that deviates from the accepted pre-established limits. When either the qSOFA score or the SIRS score reach a predetermined value, the patient is flagged as being at-risk for sepsis. The qSOFA score is defined within a range of 0-3 points. To determine the qSOFA score, the patient is assigned one point for each deviation from the following accepted pre-established limits: 1) respiratory rate greater than or equal to 22 breaths per minute, 2) systolic blood pressure less than or equal to 100 mm Hg, and 3) a change in mental status (e.g. Glasgow Coma Scale less than 15). If a patient is assigned at least 2 points on the qSOFA score, the patient is at-risk for sepsis.

The SIRS score is defined within a range of 0-4. To determine the SIRS score, the patient is assigned one point for each deviation from the following accepted pre-established limits: 1) a body temperature greater than 100.4 degrees Fahrenheit or less than 96.8 degrees Fahrenheit, 2) a heart rate greater than 90 bpm 3) a respiratory rate greater than 20 breaths per minute, and 4) a white blood cell count greater than 12,000 cells/mm$^3$, less than 4000 cells/mm$^3$, or greater than 10% immature (band) forms. If a patient is assigned at least 2 points on the SIRS score, the patient is at-risk for sepsis.

In the illustrative embodiment, the hospital bed 10 further includes at least one sensor 102 mounted to a deck section of the hospital bed 10 and a control system 104 coupled to the sensor 102 as shown in FIG. 1. The sensor 102 is configured to provide sensor signals indicative of vital signs of the patient laying on the hospital bed 10. In one embodiment, the control system 104 is configured to receive the sensor signals and compare the sensor signals to the pre-established acceptable conditions described above to determine if the patient is at-risk or should be diagnosed with sepsis. In another embodiment, the sensor signals and information stored on the patient's EMR 106 are both compared to pre-established acceptable conditions to determine if the patient is at-risk or should be diagnosed with sepsis.

In the illustrative embodiment, the sensor 102 is a non-contact vital signs monitoring sensor available from Early-Sense Inc., 135 Beaver Street Suite 307, Waltham, Mass. 02452. It provides a signal indicative of vital signs, such as, for example, a detected heart rate and a signal indicative of a detected respiration rate that is processed by the control system 104. This sensor 102 is described in greater detail in U.S. Patent Pub. No. 2018/0184984 which is expressly incorporated herein for the purpose of describing a suitable sensor used to detect patient vital signs. The sensor 102 may be mounted in multiple locations on either the fixed seat deck 32 or head deck 28 as suggested in FIG. 1. In some embodiments, multiple sensors 102 may be positioned on the fixed seat deck 32 and/or head deck 28 to provide multiple detection points with the signals from each of the multiple sensors 102 being monitored to determine an accurate vital sign signal. The use of redundant signals reduces the risk of signal loss due to movement or improper positioning of the patient on the hospital bed 10. The sensor 102 has a relatively thin thickness that permits the sensor 102 to be placed under the mattress 54 and does not interfere with the functionality or therapeutic benefit of the mattress 54. In other embodiments, a different piezoelectric sensor may be utilized in place of the sensor 102. In another embodiment, the sensor 102 may be positioned inside of the mattress 54.

In other embodiments, additional sensors may be wearable by the patient and communicatively connected to the control system 104 to provide signals indicative of vital signs of the patient. Alternatively, the wearable device or sensor may be specifically designed to detect the presence of sepsis such that the scoring methods described above are omitted and/or used in conjunction with the wearable device.

Figure 2:
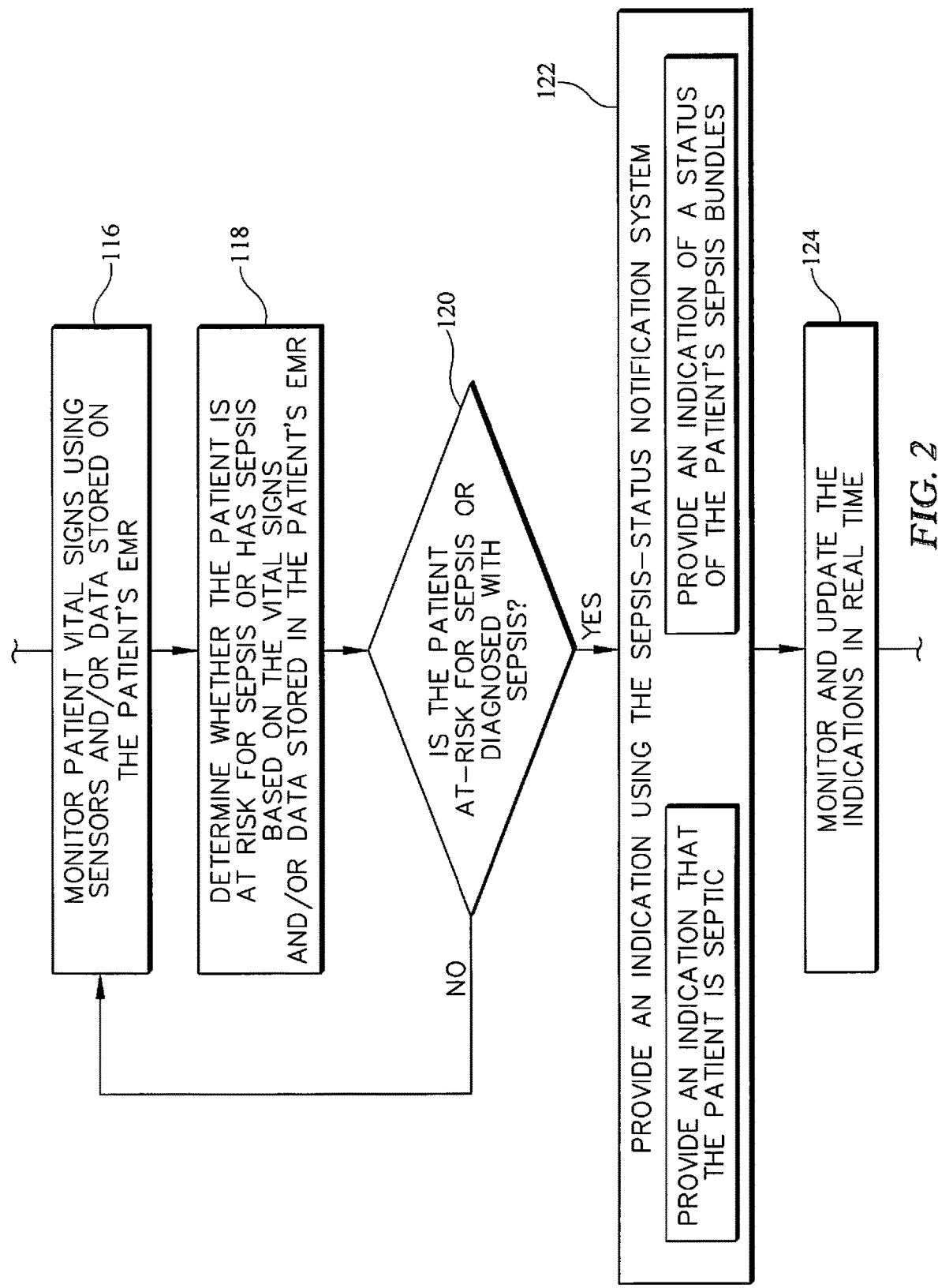
FIG. 2 is a flowchart describing a process of determining the presence of sepsis and providing an indication of the presence of sepsis using a sepsis-status notification system.

As shown in FIG. 2, the sepsis monitoring unit 100 uses the sensor 102 and the control system 104 to monitor the patient's risk for sepsis at step 116. At step 118, the sepsis monitoring unit 100 then determines whether the patient is at-risk for sepsis or should be diagnosed with sepsis based on the vital sign signals provided by the sensor 102 and the information stored on the patient's EMR 106. The vital signs and the information on EMR 106 are compared to the pre-established acceptable limits to provide a sepsis assessment score using one of the scoring methods described above or another suitable sepsis assessment method.

At step 120, the control system 104 may determine that additional tests should be performed to determine definitively if the patient is septic and send a command signal to cause the sepsis-status notification system 110 to indicate such information to a caregiver. Alternatively, the control system 104 may send a command signal as soon as the patient is determined to be at-risk for sepsis to cause the sepsis-status notification system 110 to indicate to a caregiver that the patient is septic and start monitoring the protocols.

Once the patient is determined to be at-risk or diagnosed with sepsis, the control system 104 sends a command signal to the sepsis-status notification system 110 to cause the sepsis-status notification system 110 to provide the indication to the caregiver at step 122. The indication notifies the caregiver that the patient is septic and notifies the caregiver of a status of the patient's protocols. The indication provided by the sepsis-status notification system 110 may include a visual indication or an audible indication. Additionally, the indication may be displayed on or around the hospital bed 10 or transmitted wirelessly to a remote location through the hospital network 108. At step 124, the sepsis monitoring unit 100 continues monitoring and updating the indications provided by the sepsis-status notification system 110 in real time until administration of the protocols is completed.

Figure 3:
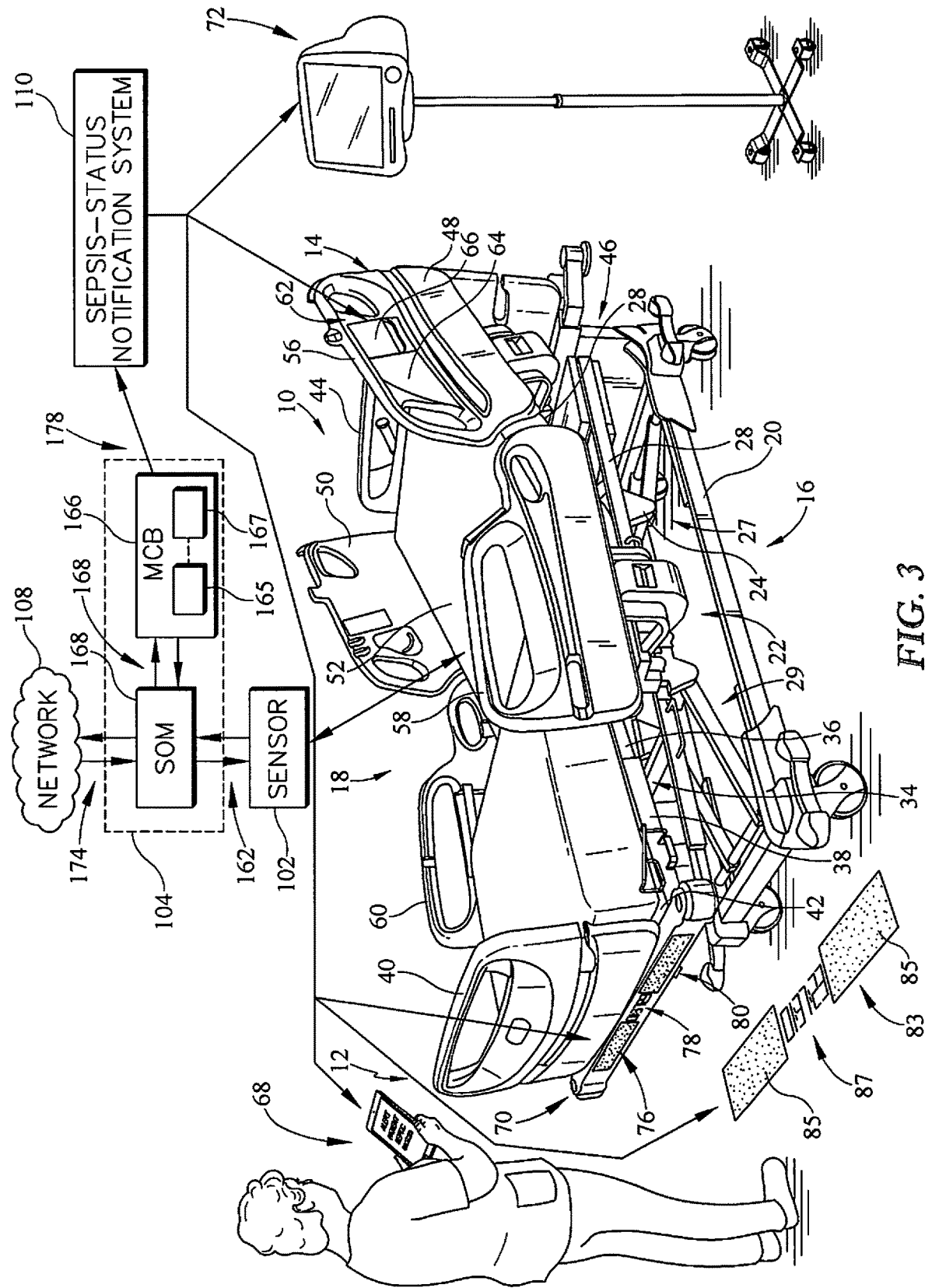
FIG. 3 is a perspective view of the patient support apparatus of FIG. 1 including a plurality of devices included in the sepsis-status notification system used to display the indication.

The view shown in FIGS. 1 and 3 is generally taken from a position that is oriented at the left side, foot end of the hospital bed 10. For purposes of orientation, the discussion of the hospital bed 10 will be based on the orientation of a patient supported on the hospital bed 10 in a supine position. Thus, the foot end 12 of the hospital bed 10 refers to the end nearest the patient's feet when the patient is supported on the hospital bed 10 in the supine position. The hospital bed 10 has a head end 14 opposite the foot end 12. A left side 16 refers to the patient's left when the patient is lying in the hospital bed 10 in a supine position. The right side 18 refers to the patient's right. When reference is made to the longitudinal length of the hospital bed 10, it refers a direction that is represented by the lines that generally extend between the head end 14 and foot end 12 of the hospital bed 10. Similarly, lateral width of the hospital bed 10 refers to a direction that is represented by the lines that generally extend between the left side 16 and right side 18.

The hospital bed 10 includes a base frame 20 which supports a lift system 22. The lift system 22 engages the base and an upper frame 24 such that the lift system 22 moves the upper frame 24 vertically relative to the base frame 20. The lift system 22 includes a head end linkage 27 and a foot end linkage 29. Each of the linkages 27 and 29 are independently is configured and may be operated to cause the hospital bed 10 to move into a tilt position which is when the head end 14 of the upper frame 24 is positioned lower than the foot end 12 of the upper frame 24. The hospital bed 10 may also be moved to a reverse tilt position with the foot end 12 of the upper frame 24 is positioned lower than the head end 14 of the upper frame 24.

The upper frame 24 supports a load frame 26. The load frame 26 supports a head deck 28 which is movable relative to the load frame 26. The load frame 26 also supports an articulated seat deck 30 (seen in FIG. 3), also movable relative to the load frame 26 and a fixed seat deck 32 (also seen in FIG. 3). Also supported from the load frame 26 is a foot deck 34 that is articulated and moveable relative to the load frame 26. The foot deck 34 in the illustrative embodiment of FIG. 1 provides for powered pivoting of the foot deck 34 and manual extension and retraction of the foot deck 34 to vary the length of the foot deck 34. In other embodiments, powered pivoting of the foot deck 34 may be omitted and the related movement may be caused manually, or follow movement of the articulated seat deck 30. In addition, in some embodiments, extension and retraction of the foot deck 34 may be powered by an actuator.

The foot deck 34 includes a first portion 36 and a second portion 38, which moves relative to the first portion 36 to vary the size of the foot deck 34. The second portion 38 moves generally longitudinally relative to the first portion 36 to vary the longitudinal length of the foot deck 34 and, thereby, the longitudinal length of the hospital bed 10.

A foot panel 40 is supported from the second portion 38 and extends vertically from an upper surface 42 of the second portion 38 to form a barrier at the foot end 12 of the hospital bed 10. A head panel 44 is positioned on an upright structure 46 of the base frame 20 and extends vertically to form a barrier at the head end 14 of the hospital bed 10. A left head siderail 48 is supported from the head deck 28 and is moveable between a raised position shown in FIG. 1 and a lowered position as is known in the art. A right head siderail 50 is also moveable between the raised position of FIG. 1 and lowered position. As shown in FIG. 1, in the raised position, the siderails 48 and 50 extend above an upper surface 52 of a mattress 54 of the hospital bed 10 when the siderails 48 and 50 are in a raised position. In a lowered position an upper edge 56 of the left head siderail 48 is below the upper surface 52.

The hospital bed 10 also includes a left foot siderail 58 and a right foot siderail 60, each of which is supported directly from the load frame 26. Each of the siderails 48, 50, 58, and 60 are is configured to be lowered to a position below the upper surface 52. It should be noted that when the head deck 28 is moved, the head siderails 48 and 50 move with the head deck 28 so that they maintain their relative position to the patient. This is because both of the head siderails 48 and 50 are supported by the head deck 28.

Referring to the left head siderail 48 shown in FIG. 12, a user interface 62 includes a hard panel 64 and a graphical user interface 66. The hard panel 64 provides indications to a user regarding the status of certain functions of the hospital bed 10 as well as providing a standard set of fixed input devices. The graphical user interface 66 includes a touchscreen display that provides information to a user as well as allowing for flexible, menu driven, operation of certain functions of the hospital bed 10. The graphical user interface 66, also known as a flip-up display (FUD), is mounted to the siderail 48 with a pivotable connection so that the graphical user interface 66 may be pivoted to allow a user the more easily view and interact with the graphical user interface 66. In some embodiments, the right head siderail 50 may include a second graphical user interface duplicative of the graphical user interface 66.

As shown in FIG. 3, the control system 104 provides all of the functionality necessary to operate the sepsis monitoring unit 100 and includes a system on a module (SOM) 164 and a master controller (MCB) 166. The sensor 102 communicates through a universal asynchronous receiver/transmitter (UART) connection 162 with the SOM 164. The SOM 164 is connected to and communicates with the MCB 166 through a UART connection 168. The SOM 164 is configured to communicate with hospital network 108 through a connection 174 and can connect to external systems, such as nurse call systems or other hospital wide communications systems such as the NaviCare® system from Hill-Rom Company, Inc., Batesville, Ind. using the hospital network 108. This allows information regarding the vital signs detected, including alarm conditions, to be transferred to other locations in the hospital or other facility in which the hospital bed 10 is located.

The sepsis-status notification system 110 displays indications that the patient is septic using a plurality of device as shown in FIGS. 3-5D. The MCB 166 communicates with each device through a connection 178 or wirelessly using the SOM 164 and the hospital network 108. The connection 178 may be a simple UART interface, a CAN interface, a discrete wiring connection, or any other suitable connection. Each of the connections 162, 168, 170, 174, 178, and 184 may be a simple UART interface, a CAN interface, a discrete wiring connection, or any other suitable connection as required for the particular application. Relative to the sepsis-status notification system 110, the MCB 166 includes a processor 165 and a non-transitory memory device 167 that stores instructions. When appropriate, the instructions are executed to operate the sepsis monitoring unit 100 and display the indications. Some of the processing and instructions may be resident on the SOM 164 as it relates to specific tasks to be executed under the direction of the MCB 166.

As shown in FIG. 3, the sepsis-status notification system 110 can display the indications using the graphical user interface 66, a mobile device 68 used by the caregiver, an indicator panel 70 on the hospital bed 10, and/or one or more monitors 72 located in the room where the hospital bed 10 and the patient are located. The mobile device 68 is illustratively embodied as a tablet, such as an iPad®, that is carried by the caregiver during rounds. The indicator panel 70 is coupled to the foot end 12 of the hospital bed 10, but may be located on any part of the hospital bed 10 that is easily viewable. The monitor 72 is illustratively embodied as a vitals monitor but may also include a computer monitor or a television screen located in the room. Other devices located in a remote location, such as, for example, a nurse call station, may also be used.

In one example, when the SIRS, qSOFA, or other sepsis assessment score is below their predetermined values, the notification system 110 may cause the devices to display a green color to signal to the caregiver that the patient does not have sepsis. Once either of the SIRS, qSOFA, or another sepsis assessment score exceeds their predetermined value, the notification system 110 may cause the devices to display a red color to signal that the patient has been diagnosed with sepsis and action is needed. In some embodiments, the notification system 110 projects an image 83 and the colors on the floor around the hospital bed so that a caregiver may be able to see the data in real time at a distance. In other embodiments, the image 83 and/or the colors may be flashed in the appropriate respective color.

Figure 4B:
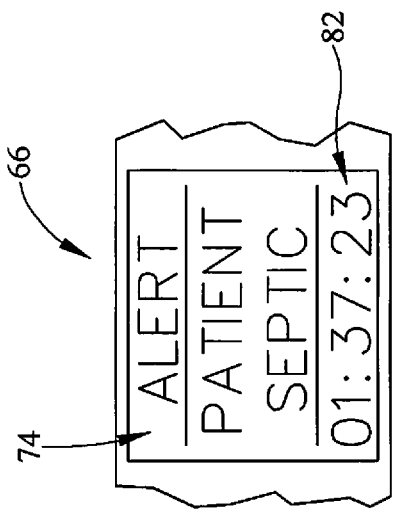
FIG. 4B is an enlarged view of a mobile device held by a caregiver displaying a visual indication that the patient is septic.
Figure 4D:
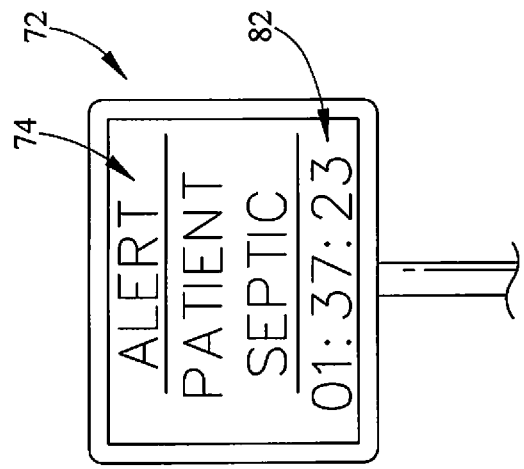
FIG. 4D is an enlarged view of an external monitor displaying a visual indication that the patient is septic.
Figure 4A:
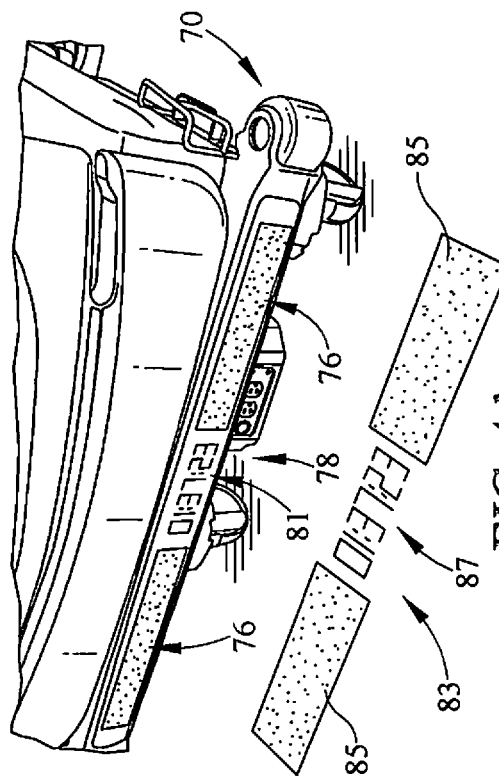
FIG. 4A is an enlarged view of an indicator panel coupled to the patient support apparatus displaying a visual indication that the patient is septic.
Figure 4C:
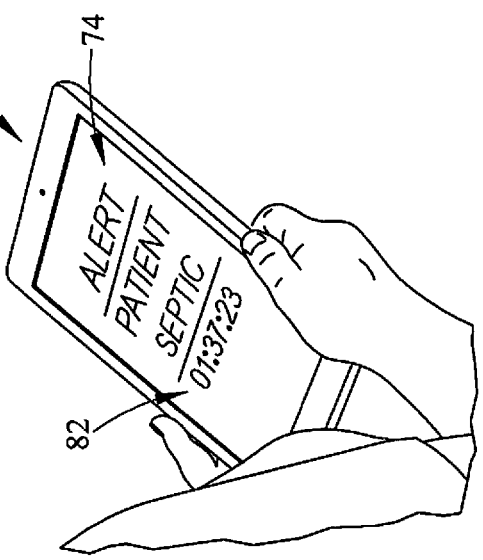
FIG. 4C is an enlarged view of graphical user interface on a side rail of the patient support apparatus displaying a visual indication that the patient is septic.

As shown in FIGS. 3 and 4A, the indicator panel 70 is configured to display several visual indications that indicate that the patient is septic and action is needed. The indicator panel 70 includes a first section 76 with a light that is displayed in a first color prior to the patient being diagnosed with sepsis. Once the patient has been diagnosed with sepsis, the MCB 166 is configured to send a command signal to display the light on the indicator panel 70 in a second color that is different than the first color. The second color notifies the caregiver than the patient is septic and action is needed. The indicator panel 70 further includes a second section 78 that is configured to display a timer 81 indicating an amount of time remaining in the sepsis protocols. The location of the indicator panel 74 makes the statuses of the conditions easily discernable from a distance, such that a caregiver may quickly ascertain the statuses from the hallway or the door of a patient's room. The indicator panel 70 may further include one or more projectors 80 for projecting the image 83 including a light 85 and a timer 87 on the floor around the hospital bed 10. The light 85 may have a first color, such as green, to indicate an absence of sepsis and a second color, such as red or amber, to indicate that the patient has been diagnosed with sepsis. An example of a suitable projector is described in U.S. Patent Pub. No. 2018/0184984 which is expressly incorporated by reference herein for the description of a suitable projector that can project images and/or light on a surface.

The timer 87 is illustratively embodied as a countdown timer 87 that begins counting at the time the sepsis monitoring unit 100 first determines that the patient is septic. However, in another embodiment, the timer 87 may measure time elapsed after the sepsis monitoring unit 100 first determines that the patient is septic. The timer 87 may count down from three hours indicating that the patient is within the sepsis three hour protocol administration. After completion of the three hour protocol administration the control system 104 may update the timer 87 to track the sepsis six hour protocol administration. The control system 104 may issue additional indications during protocol administration to remind caregivers of actions that need to be completed within each protocol. In some embodiments, the additional indications are provided in response to the timer 87 reaching a predetermined time in the protocol. In other embodiments, the additional indications are provided in response to updates in the patient's treatment of sepsis, such as, for example, upon completion of one of the actions required during protocol administration.

As shown in FIGS. 3 and 4B-4D, the sepsis-status notification system 110 may also use the other devices 66, 68, and 72 to indicate that the patient is septic and action is needed. The MCB 166 is configured to send a command signal to one or more of the devices 66, 68, 72 to cause the devices to display an alert message 74 when the patient is diagnosed with sepsis. The MCB 166 may also send a command signal to one or more of the devices 66, 68, 72 to cause the devices to provide an audible alert to notify the caregiver to check the device or to audibly convey the alert message 74. The alert message 74 includes information indicating to the caregiver that the patient is septic and information related to the status of the sepsis protocols administration. For example, each time the patient is scanned during rounds or connected to a new device with a monitor, the MCB 166 is configured to send the command signal to the device to cause the alert message 74 to be displayed. Additionally, the alert message 74 may be displayed multiple times during protocol administration to remind caregivers of actions to be taken as described above.

Figure 5:
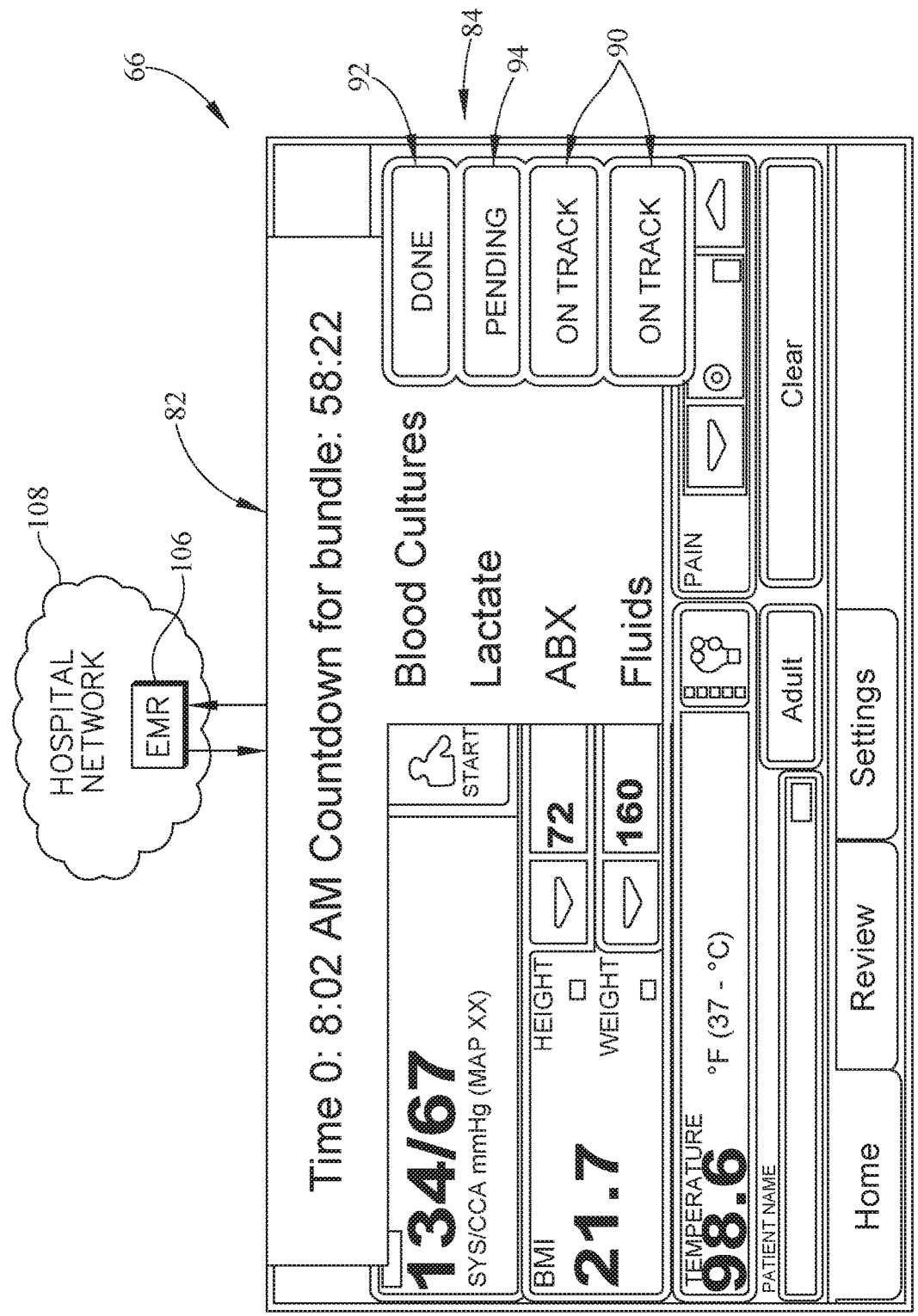
FIG. 5 is another enlarged view of the graphical user interface displaying an action list with statuses for each procedure that should be competed after the patient is diagnosed with sepsis.
Figure 6:
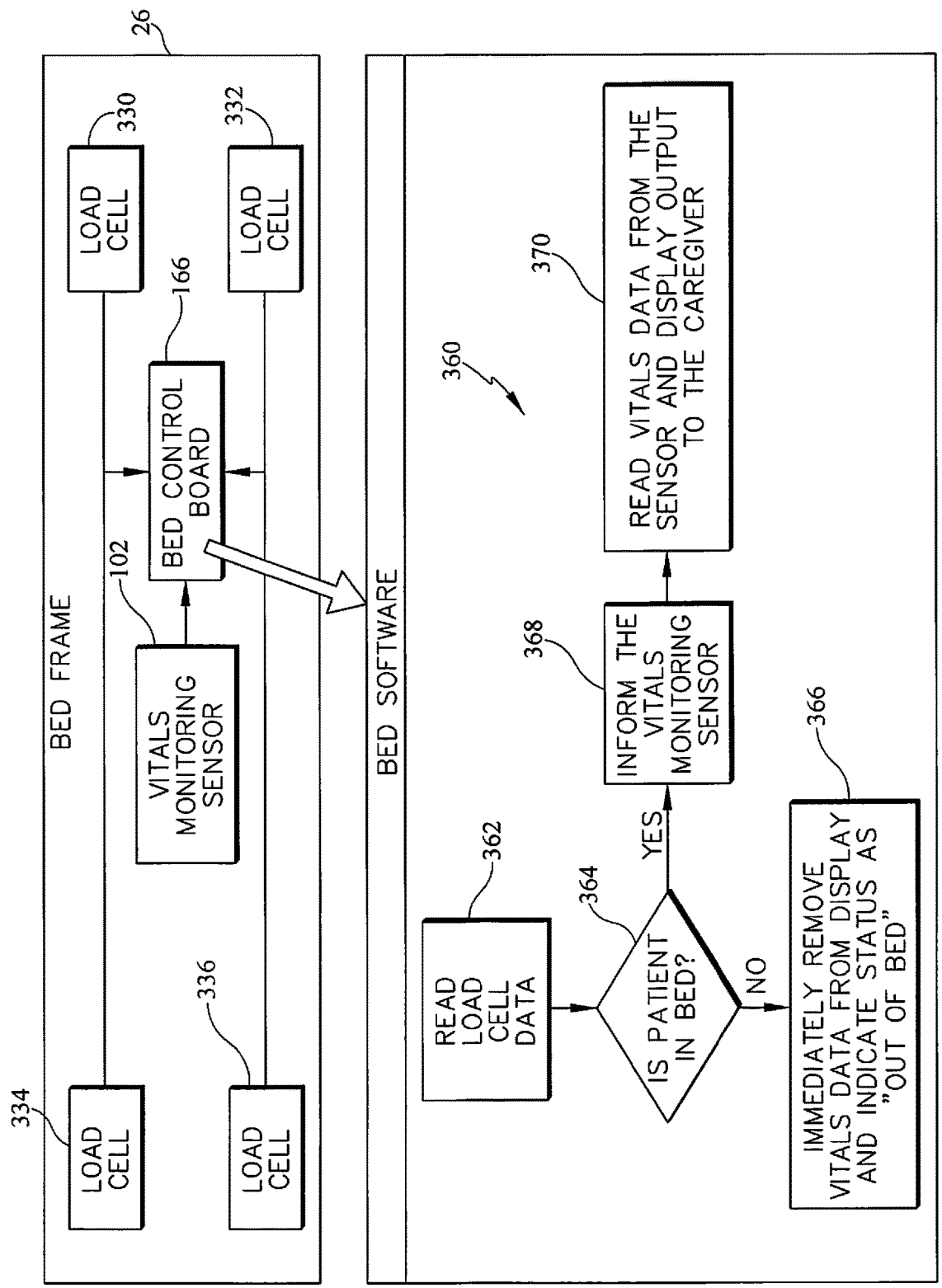
FIG. 6 is a diagrammatic view of portion of the patient support apparatus along with a related flowchart.

As shown in FIG. 5, the illustrative alert message 74 displayed on the screen of each device 66, 68, 72 includes information that helps the caregiver determine what actions are needed for compliance with the sepsis protocols. The alert message 74 includes a timer 82 and an action list 84. The timer 82 is similar to timer 87 and includes the time when the patient was first diagnosed with sepsis (i.e. time 0) and a countdown timer displaying an amount of time remaining for one or more of the protocols to be completed. The action list 84 includes a list of all of the actions that should be taken in the protocols and the status of each action. The action list 84 displays the status of each of these action in real time. The caregiver may manually update the action list 84 by changing the status in the alert message 74. Alternatively, the action list 84 may be updated automatically as the control system 104 communicates with the hospital network 108 or another wireless device and the actions are completed.

The action list 84 may display the status of each of the actions in several different ways as shown in FIG. 5. If an action still needs to be completed, the alert message 74 displays a first representation 90 to indicate to a caregiver that action is still needed. Once the action is completed, the alert message 74 displays a second representation 92 that the action no longer needs to be completed. The first representation 90 may include an icon, color, and/or text that indicate to the caregiver that action is needed. Conversely, the second representation 92 may include a different icon, color, and/or text from the first representation that indicate to the caregiver that no action is needed. Some actions may have a period of time during which their status is pending, such as, for example, when results are pending after a test is completed. In those instances, the alert message 74 displays a third representation 94 with a different icon, color, and/or text from the first and second representations 90, 92 indicating that the status is pending.

As shown in FIG. 5, the device 66 is also configured to display other information in additional to the alert message 74 and/or the action list 84. The additional information may include the patient's vitals, other patient information, and/or information related to the hospital bed 10. The information related to the hospital bed may include a position of the one or more sections of the hospital bed 10 and an indication of features that are included the hospital bed 10.

In operation, the notification system 110 is configurable to allow or prevent the indication capabilities of the devices 66, 68, 70, 72. A caregiver may choose to disable the devices in the notification system 110 when the caregiver determines that the operation of the devices 66, 68, 70, 72 is unnecessary or would be problematic with a particular patient. In an effort to avoid unnecessary alert conditions, detection and notification system 160 utilizes a process 360 shown in FIG. 7 to determine whether an alert condition is warranted. The signals from the load cells 330, 332, 334, and 336 are provided to the bed controller 166 which makes a determination from the signals, using process 360. At process step 362, the controller 166 reads the load cell data. The load cell data is then analyzed at a decision step 364 to determine if a patient is supported on the bed. If the patient is determined not to be in the bed at decision step 364, then the controller 166 proceeds to step 366, overrides the heart rate and respiration rate alert conditions, and provides a message on the graphical user interface 66 that the patient is out of the bed 10.

In some cases, the notification system 110 may go into an alert state relative to the patient exiting the bed as disclosed in the PCT application WO2016/196403 which is expressly incorporated by reference for the teaching of a patient exit detection system. However, alerts related to vital signs would be invalid and, in embodiments where the process 360 is applied, will cause the alerts to be ignored. However, if the patient is determined to be in bed at step 364, the controller 166 proceeds to step 368 and informs the notification system 110 that vital signals are expected from the sensor 102. The process 360 then proceeds to step 370 and the notification system 110 operates normally.

In some embodiments, the controller 166 may determine from the load cells 330, 332, 334, and 336 that a patient is in a particular location on the bed 10. If more than one sensor 102 is present on the bed 10, then the controller 166 may use the information regarding the patient location to discount one or more of the sensor 102 signals to ensure that the best signal is being considered in the determination of the vital signs. In addition, the controller 166 may consider the angle of the head deck 28 in making the determination as to which of multiple sensors 102 should be used in the analysis. For example, if the head deck 28 is raised to an extreme angle, then a sensor 102 positioned in a back section may be discounted or disregarded.

Although certain illustrative embodiments have been described in detail above, variations and modifications exist within the scope and spirit of this disclosure as described and as defined in the following clauses and claims.

The invention claimed is:

1. A patient support apparatus comprising
a sensor providing signals indicative of vital signs of a patient positioned on the patient support apparatus,
a controller coupled to the sensor and including a processor and a memory device, the memory device including instructions that, when executed, cause the controller to receive the signals, compare the signals to pre-established acceptable limits, calculate a sepsis risk assessment score based on the signals, and, if the sepsis risk assessment score is at or above a predetermined value, output a command signal to initiate a sepsis protocol administration, and
a sepsis-status notification system responding to the command signal from the controller to display a first visual indication that shows that the patient is septic and display second visual indication that shows a status of the sepsis protocol administration,
wherein the status of the sepsis protocol administration includes an action list having a first action associated with the sepsis protocol administration, a second action associated with the sepsis protocol administration, and a third action associated with the sepsis protocol administration, and
wherein the first action includes a first status having a first representation configured to indicate that action is still needed, the second action includes a second status having a second representation configured to indicated that no action is needed, and the third action includes a third status having a third representation configured to indicated that the third action is pending.

2. The patient support apparatus of claim 1, wherein the first visual indication includes an alert that shows the patient is septic and the second visual indication includes a timer that measures how long the patient has been septic.

3. The patient support apparatus of claim 2, wherein the timer is a countdown timer that displays an amount of time remaining in the sepsis protocol administration.

4. The patient support apparatus of claim 2, wherein the controller is configured to communicate with an external nurse call station and the visual indications are transmitted for display at a nurse call station.

5. A hospital bed comprising
a frame,
a sensor providing signals indicative of vital signs of a patient positioned on the frame,
a controller coupled to the sensor and including a processor and a memory device, the memory device including instructions that, when executed, cause the controller to receive the signals, compare the signals to pre-established acceptable limits, calculate a sepsis risk assessment score based on the signals, and, if the sepsis risk assessment score is at or above a predetermined value, output a command signal to initiate a sepsis protocol administration, and
a sepsis-status notification system responding to the command signal from the controller to display a first visual indication that shows that the patient is septic and display second visual indication that shows a status of the sepsis protocol administration,
wherein the sepsis-status notification system includes a projector coupled to the frame and configured to project the first visual indication on a floor around the frame, the first visual indication includes a countdown timer that indicates an amount of time remaining in the sepsis protocol administration.

6. The patient support apparatus of claim 1, wherein the at least one of the first and the second visual indications includes an alert message on an interface coupled to the patient support apparatus.

7. The patient support apparatus of claim 6, wherein the alert message includes at least one of a textual indication that the patient is septic, an iconic representation that the patient is septic, and a timer.

8. The patient support apparatus of claim 1, wherein at least one of the first and the second visual indications includes an indicator panel coupled to the patient support apparatus that has a first color when no command signal is provided and has a second color, different from the first color when the command signal is provided.

9. The patient support apparatus of claim 1, wherein the controller is configured to communicate with an electronic medical record system to receive information from the electronic medical record system indicative of a medical history of a patient supported on the patient support apparatus.

10. The patient support apparatus of claim 9, wherein the controller is configured to compare the signals provided by the sensor to a list of predetermined conditions stored in the electronic medical record system to determine if the patient is septic.

11. The patient support apparatus of claim 10, wherein the controller is configured to provide the command signal if at least one of the vital signs deviates from acceptable limits and at least one of the predetermined conditions is present in the patient's electronic medical record.

12. The patient support apparatus of claim 9, wherein the controller is configured to compare the predetermined conditions to pre-established acceptable limits and provide the command signal when at least one vital sign deviates from an acceptable limit and at least one predetermined condition deviates from the acceptable limit.

13. The patient support apparatus of claim 12, wherein the predetermined condition includes at least one of low blood pressure and a change in mental status.

14. A hospital bed comprising
- a frame,
- a first sensor providing a first signal indicative of a first vital sign of a patient supported on the patient support apparatus and a second sensor providing a second signal indicative of a second vital sign of the patient different than the first vital sign indicated by the first sensor,
- a controller coupled to the sensors and including a processor and a memory device, the memory device including instructions that, when executed, cause the controller to receive the first and second sensor signals, analyze an electronic medical record storing patient information for the patient, compare the signals and the patient information to pre-established acceptable limits, calculate a sepsis risk assessment score based on the signals and the patient information, and, if the sepsis risk assessment score is at or above a predetermined value, output a command signal to initiate a sepsis protocol administration, and
- a notification system responding to the command signal from the controller, the notification system including an interface coupled to the frame and configured to provide at least ene a first visual indication that shows that the patient is septic, and indicator panel coupled to the frame and configured to provide a second visual indication that shows that the patient is septic, and a projector coupled to the frame and configured to project a third visual indication onto a surface spaced apart from the frame that shows that the patient is septic,
- wherein the first visual indication includes an alert that shows the patient is septic and a timer that indicates how long the patient has been septic, the second visual indication includes a color that indicates that the patient is septic and a second timer that indicates how long the patient has been septic, and the third visual indication includes the color and a third timer that indicates how long the patient has been septic.

15. The hospital bed of claim 14, wherein the first visual indication further includes a status of the sepsis protocol administration in real time.

16. The hospital bed of claim 14, wherein the timer is a countdown timer that shows an amount of time remaining in the sepsis protocol administration.

17. The hospital bed of claim 16, wherein the first visual indication further includes a display of the procedures performed on the patient since sepsis was determined to be present.

18. The hospital bed of claim 14, wherein the color is displayed on each side of the second timer and the third timer.

19. The hospital bed of claim 5, wherein the status of the sepsis protocol administration includes an action list having a first action associated with the sepsis protocol administration, a second action associated with the sepsis protocol administration, and a third action associated with the sepsis protocol administration, and
- wherein the first action includes a first status having a first representation configured to indicate that action is still needed, the second action includes a second status having a second representation configured to indicated that no action is needed, and the third action includes a third status having a third representation configured to indicated that the third action is pending.

20. The hospital bed of claim 5, wherein the controller is configured to diagnose the patient as being septic and the first visual indication further includes a color that is displayed on each side of the timer to indicate that the patient is septic.

* * * * *

UNITED STATES PATENT AND TRADEMARK OFFICE
CERTIFICATE OF CORRECTION

PATENT NO. : 11,653,872 B2
APPLICATION NO. : 16/795666
DATED : May 23, 2023
INVENTOR(S) : Stacey A. Fitzgibbons et al.

It is certified that error appears in the above-identified patent and that said Letters Patent is hereby corrected as shown below:

In the Claims

Column 13, Line 29, Claim 14, after "configured to provide" delete "at least ene"

Signed and Sealed this
Nineteenth Day of September, 2023

Katherine Kelly Vidal
Director of the United States Patent and Trademark Office